United States Patent
Patel et al.

(10) Patent No.: US 11,918,590 B2
(45) Date of Patent: *Mar. 5, 2024

(54) STABLE EXTENDED RELEASE PHARMACEUTICAL COMPOSITION OF CLOZAPINE

(71) Applicant: Intas Pharmaceuticals Ltd., Ahmedabad (IN)

(72) Inventors: Rikin Patel, Ahmedabad (IN); Kavan Pandya, Ahmedabad (IN); Piyush Kansagra, Ahmedabad (IN); Satyavan Dhavale, Ahmedabad (IN); Ashish Sehgal, Ahmedabad (IN)

(73) Assignee: Intas Pharmaceuticals Ltd., Ahmedabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 17/716,694

(22) Filed: Apr. 8, 2022

(65) Prior Publication Data
US 2023/0181595 A1 Jun. 15, 2023

(30) Foreign Application Priority Data
Dec. 15, 2021 (IN) .............................. 202121058299

(51) Int. Cl.
*A61K 31/5513* (2006.01)
*A61K 9/20* (2006.01)
*A61K 9/48* (2006.01)

(52) U.S. Cl.
CPC ............ *A61K 31/5513* (2013.01); *A61K 9/20* (2013.01); *A61K 9/48* (2013.01)

(58) Field of Classification Search
CPC .................................................. A61K 31/5513
See application file for complete search history.

(56) References Cited

U.S. PATENT DOCUMENTS

| 2012/0058993 A1* | 3/2012 | Surman .............. A61K 31/5513 514/220 |
| 2015/0283092 A1* | 10/2015 | Ruddy ...................... A61K 9/50 |
| 2020/0054573 A1* | 2/2020 | Saxena .................... A61K 9/50 |

FOREIGN PATENT DOCUMENTS

| RU | 2414903 C1 | 10/2009 |
| WO | 2006059194 A2 | 6/2006 |
| WO | 2017142438 A1 | 8/2017 |
| WO | 2018051292 A1 | 3/2018 |

OTHER PUBLICATIONS

Merriam-Webster, Assay Definition & Meaning, downloaded in Jun. 2022 (Year: 2022).*

* cited by examiner

*Primary Examiner* — Mark V Stevens
*Assistant Examiner* — Alparslan Asan
(74) *Attorney, Agent, or Firm* — McAndrews, Held & Malloy, Ltd.

(57) ABSTRACT

Disclosed are stable extended release formulations and pharmaceutical compositions of Clozapine that exhibit improved stability under a variety of conditions, as well as processes for the preparation of such formulations and compositions.

8 Claims, No Drawings

STABLE EXTENDED RELEASE PHARMACEUTICAL COMPOSITION OF CLOZAPINE

RELATED APPLICATIONS

This application is related to and claims priority to Indian Patent Application No. 202121058299, filed Dec. 15, 2021, which is incorporated by reference herein in its entirety.

FIELD OF THE INVENTION

The present invention relates to a stable extended release pharmaceutical composition of Clozapine and processes for preparation thereof, wherein the pharmaceutical composition provides improved stability.

BACKGROUND

Clozapine is classified as an "atypical" antipsychotic drug. The chemical name for Clozapine is 8-chloro-11-(4-methyl-1-piperazinyl)-5H-dibenzo [b,e][1,4] diazepine with the following structure (Formula I):

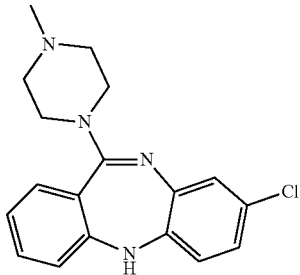

(Formula I)

Clozapine

Clozapine is a yellow, crystalline powder, very slightly soluble in water. The molecular formula is $C_{18}H_{19}ClN_4$ and the molecular weight is 326.83.

Clozapine is used for the management of severely ill schizophrenic patients who fail to respond adequately to standard drug treatment for schizophrenia. Clozapine is also used for reducing the risk of recurrent suicidal behavior in patients with schizophrenia or schizoaffective disorder who are judged to be at chronic risk for re-experiencing suicidal behavior, based on history and recent clinical state. Clozapine is also used in the treatment of Parkinson related psychosis. Suicidal behavior refers to actions by a patient that put him/herself at risk for death.

Clozapine was first disclosed in the U.S. Pat. No. 3,539,573 patent and is classified as an atypical anti-psychotic agent. Clozapine is marketed by Novartis in the US as CLOZARIL® immediate release tablets.

The mean terminal half-life of Clozapine is 12 hours, so multiple dosing is required to maintain steady state. Thus, it is desirable to develop a sustained release formulation of Clozapine. The half-life of Clozapine causes peaks and fluctuations in its blood concentration, which leads to problems associated with toxicity and patient compliance due to multiple dosing requirements to maintain steady state. Extended release dosage form for once-a-day dosing regimen shall increase the therapeutic efficacy, reduce the fluctuations in drug concentration in the blood and shall provide patient compliance.

SUMMARY

The object of the present invention is to provide a stable extended release pharmaceutical composition of Clozapine, wherein the pharmaceutical composition provides improved stability.

Another object of the present invention is to provide a stable extended release pharmaceutical composition of Clozapine, wherein the individual impurity level in the pharmaceutical composition is not more than 0.2% w/w of Clozapine upon storage at 40±2° C. and 75±5% RH for 6 months.

Another object of the present invention is to provide a stable extended release pharmaceutical composition of Clozapine, wherein the total impurities in the pharmaceutical composition is not more than 2% w/w of Clozapine upon storage at 40±2° C. and 75±5% RH for 6 months.

Another object of the present invention is to provide a stable extended release pharmaceutical composition of Clozapine, wherein the assay of Clozapine is 95% to 105% after storage at 40° C. and 75% RH for 6 months.

Another object of the present invention is to provide a stable extended release pharmaceutical composition of Clozapine, wherein the composition provides dissolution profile as: (1) not more than 30% weight of Clozapine is dissolved in 30 minutes; (2) between 40% to 70% weight of Clozapine is dissolved in 2 hours; and (3) more than 80% weight of Clozapine is dissolved in 10 hours.

Another object of the present invention is to provide a stable extended release pharmaceutical composition of Clozapine, wherein the individual impurity level in the composition is not more than 0.2% w/w of Clozapine upon storage at 25±2° C. and 60±5% RH for 6 months.

Another object of the present invention is to provide a stable extended release pharmaceutical composition of Clozapine, wherein the total impurities in the pharmaceutical composition is not more than 2% w/w of Clozapine upon storage at 25±2° C. and 60±5% RH for 6 months.

Another object of the present invention is to provide a stable extended release pharmaceutical composition of Clozapine, wherein the assay of Clozapine is 95% to 105% after storage at 25±2° C. and 60±5% RH for 6 months.

Another object of the present invention is to provide a stable extended release pharmaceutical composition of Clozapine, wherein the composition comprises Clozapine having an effective average particle size (D90) of less than about 10 micron that provides solubility of Clozapine of at least 20 mg/ml in 0.1N Hydrochloric acid (HCl).

In an aspect, the disclosure provides a stable extended release pharmaceutical composition comprising Clozapine and one or more pharmaceutically acceptable excipients, wherein the composition exhibits stability upon storage at 40±2° C. and 75±5% RH for 6 months. In embodiments of this aspect, the total impurities in the pharmaceutical composition is not more than 2% w/w of Clozapine upon storage at 40±2° C. and 75±5% RH for 6 months. In embodiments of this aspect, the individual impurity level in the pharmaceutical composition is not more than 0.2% w/w of Clozapine upon storage at 40±2° C. and 75±5% RH for 6 months. In embodiments of this aspect, an assay of Clozapine in the pharmaceutical composition is from 95% to 105% upon storage at 40±2° C. and 75±5% RH for 6 months.

In another aspect, the disclosure provides a stable extended release pharmaceutical composition comprising Clozapine and one or more pharmaceutically acceptable excipients, wherein the composition exhibits stability upon storage at 25±2° C. and 60±5% RH for 6 months. In embodiments of this aspect, the total impurities in the pharmaceutical composition is not more than 2% w/w of Clozapine upon storage at 25±2° C. and 60±5% RH for 6 months. In embodiments of this aspect, the individual impurity level in the pharmaceutical composition is not more than 0.2% w/w of Clozapine upon storage at 25±2° C. and 60±5% RH for 6 months. In embodiments of this aspect, an assay of Clozapine in the pharmaceutical composition is from 95% to 105% upon storage at 25±2° C. and 60±5% RH for 6 months.

In another aspect, the disclosure provides a stable extended release pharmaceutical composition comprising Clozapine and one or more pharmaceutically acceptable excipients, wherein the composition provides dissolution profile as: (1) not more than 30% weight of Clozapine is dissolved in 30 minutes; (2) between 40% to 70% weight of Clozapine is dissolved in 2 hours; and (3) more than 80% weight of Clozapine is dissolved in 10 hours, wherein the dissolution profile is measured using a USP type I apparatus (basket), placing the composition in 900 ml of acetate buffer having pH 4.5 at 37° C. and 100 rpm.

In some embodiments of this aspect, the composition comprising multiparticulates that comprise: a) granules, pellets, beads or spheroids comprising Clozapine, b) a first seal coat layer, c) an acidic coating with acidic substance, d) a second seal coat layer, (e) an extended release coating with a water insoluble polymer and a water soluble polymer and (f) a third seal coat layer.

In some embodiments of this aspect, the stable extended release pharmaceutical composition is compressed in the form of tablets or mini-tablets, or filled in capsules for oral administration.

In some embodiments of this aspect, the total impurities in the pharmaceutical composition is not more than 2% w/w of Clozapine upon storage at 40±2° C. and 75±5% RH for 6 months.

In some embodiments of this aspect, the individual impurity level in the pharmaceutical composition is not more than 0.2% w/w of Clozapine upon storage at 40±2° C. and 75±5% RH for 6 months.

In some embodiments of this aspect, the total impurities in the pharmaceutical composition is not more than 2% w/w of Clozapine upon storage at 25±2° C. and 60±5% RH for 6 months.

In some embodiments of this aspect, the individual impurity level in the pharmaceutical composition is not more than 0.2% w/w of Clozapine upon storage at 25±2° C. and 60±5% RH for 6 months.

In some embodiments of this aspect, an assay of Clozapine in the pharmaceutical composition is from 95% to 105% upon storage at 25±2° C. and 60±5% RH for 6 months.

In some embodiments of this aspect, an assay of Clozapine in the pharmaceutical composition is from 95% to 105% upon storage at 40±2° C. and 75±5% RH for 6 months.

In further embodiments of any of the above aspects and embodiments, the composition comprises Clozapine having an effective average particle size (D90) of less than about 10 micron that provides solubility of Clozapine of at least 20 mg/ml in 0.1N Hydrochloric acid.

In a preferred embodiment, the present invention comprises a stable extended release pharmaceutical composition of Clozapine with one or more pharmaceutically acceptable excipients, wherein the total impurities in the said pharmaceutical composition is not more than 2% w/w of Clozapine and wherein the assay of Clozapine in the said pharmaceutical composition is from 95% to 105% upon storage at 40±2° C. and 75±5% RH for 6 months.

In a preferred embodiment, the present invention comprises a stable extended release pharmaceutical composition of Clozapine with one or more pharmaceutically acceptable excipients, wherein the total impurities in the said pharmaceutical composition is not more than 2% w/w of Clozapine and wherein the assay of Clozapine in the said pharmaceutical composition is from 95% to 105% upon storage at 25±2° C. and 60±5% RH for 6 months.

A stable extended release pharmaceutical composition of Clozapine with one or more pharmaceutically acceptable excipients, wherein the total impurities in the said pharmaceutical composition is not more than 2% w/w of Clozapine and wherein the assay of Clozapine in the said pharmaceutical composition is from 95% to 105% upon storage at 25±2° C. and 60±5% RH for 6 months.

Other aspects and embodiments will be apparent to those of skill in the art upon review of the following detailed description.

DETAILED DESCRIPTION

The present invention provides a stable extended release pharmaceutical composition of Clozapine, wherein the pharmaceutical composition provides improved stability under a variety of conditions (e.g., storage conditions). Clozapine is known to have poor solubility and stability at neutral conditions, and cannot be formulated as a solution. While various attempts have been made to provide improved or alternative Clozapine compositions, the need remains to provide Clozapine compositions (e.g., pharmaceutical compositions) having at least one of an improved dissolution profile, bioavailability, and/or stability. Such pharmaceutical compositions play an important role in determining a drug's market acceptance and success.

Further, extended release dosage forms of Clozapine have been shown to be difficult to develop at least with regard to maintaining an extended release profile along with good Clozapine stability. For example, the art has failed to demonstrate stability data of an ER Clozapine composition under different temperature/humidity conditions and time periods.

Accordingly, the disclosure provides a stable extended release pharmaceutical composition of Clozapine, wherein the pharmaceutical composition provides improved stability of Clozapine under a variety of conditions.

In some embodiments, the disclosure relates to a stable extended release pharmaceutical composition of Clozapine, wherein the composition comprises an effective average particle size of Clozapine (D90) of less than about 10 micron that provides solubility of at least 20 mg/ml in 0.1 N Hydrochloric acid.

In a first embodiment, the present invention relates to a stable extended release pharmaceutical composition of Clozapine, wherein the pharmaceutical composition provides improved stability.

In another embodiment, the present invention relates to a stable extended release pharmaceutical composition of Clozapine, wherein the individual impurity level in the pharmaceutical composition is not more than 0.2% w/w of Clozapine upon storage at 40±2° C. and 75±5% RH for 6 months.

In another embodiment, the present invention relates to a stable extended release pharmaceutical composition of Clozapine, wherein the total impurities in the pharmaceutical composition is not more than 2% w/w of Clozapine upon storage at 40±2° C. and 75±5% RH for 6 months.

In another embodiment, the present invention relates to a stable extended release pharmaceutical composition of Clozapine, wherein the assay of Clozapine is from 95% to 105% after storage at 40° C. and 75% RH for 6 months.

In another embodiment, the present invention relates to a stable extended release pharmaceutical composition of Clozapine, wherein the composition provides dissolution profile as: (1) not more than 30% weight of Clozapine is dissolved in 30 minutes; (2) between 40% to 70% weight of Clozapine is dissolved in 2 hours; and (3) more than 80% weight of Clozapine is dissolved in 10 hours after storage, wherein the dissolution profile is measured using a USP type I apparatus (basket), placing the composition in 900 ml of acetate buffer having pH 4.5, at 37° C. and 100 rpm.

In another embodiment, the present invention relates to a stable extended release pharmaceutical composition of Clozapine, wherein the individual impurity level in the composition is not more than 0.2% w/w of Clozapine upon storage at 25±2° C. and 60±5% RH for 6 months.

In another embodiment, the present invention relates to a stable extended release pharmaceutical composition of Clozapine, wherein the total impurities in the pharmaceutical composition is not more than 2% w/w of Clozapine upon storage at 25±2° C. and 60±5% RH for 6 months.

In another embodiment, the present invention relates to a stable extended release pharmaceutical composition of Clozapine, wherein the assay of Clozapine is from 95% to 105% after storage at 25±2° C. and 60±5% RH for 6 months.

In another embodiment, the present invention relates to a stable extended release pharmaceutical composition of Clozapine, wherein the composition comprises Clozapine having an effective average particle size (D90) of less than about 10 micron that provides solubility of at least 20 mg/ml in 0.1 N HCl.

Definitions

The term "Clozapine" used throughout the specification refers to not only Clozapine free base, but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof.

The term "Extended release pharmaceutical composition" as used herein before and throughout the description refers to drug delivery system releasing clozapine at a predetermined rate, locally or systemically, for a specified period of time. Extended release can be used interchangeably with prolonged release, programmed release, timed release, sustained release, controlled release, and modified release, slow release and other such dosage forms. The present invention relates to extended release pharmaceutical composition of clozapine, wherein the pharmaceutical composition is in the form of granules, pellets, beads, spheroids of the likes thereof, and the pharmaceutical composition are dispensed or compressed in the form of tablets or mini-tablets, or filled in capsules to provide extended release composition of clozapine for oral administration.

The term "seal coat" is synonymous to various terms like separating layer, seal coating layer, intermediate layer, barrier coating layer, film coating and the like. The seal coat comprises the substances but not limited to water-soluble substance or water-insoluble substance; one or more pharmaceutically acceptable excipient(s). Preferably, the seal coat comprises hydrophilic polymer such as HPMC or hypromellose.

The term "extended release coat" mainly comprises of extended release polymers and optionally other pharmaceutically acceptable excipients; wherein the extended release coat prolongs the release of Clozapine. Specifically the extended release coat comprises a water insoluble polymer and a water soluble polymer, wherein the water soluble polymer act as pore former and/or a plasticizer.

Suitable "polymers" may include water soluble and water insoluble polymers. Suitable polymers may include one or more of cellulosic polymers/copolymers or its derivatives including methyl cellulose, hydroxypropyl methylcellulose (HPMC or hypromellose), hydroxyethyl cellulose, hydroxypropyl cellulose, hydroxyethyl methylcellulose, carboxymethylcellulose, sodium carboxymethylcellulose, polyethylene glycol, PEG 400, polyethylene oxides, chitosan, gums, starch derivatives, polyurethanes, polysaccharides, polyalcohols, cellulose derivatives as ethyl cellulose, ethyl cellulose aqueous dispersion, cellulose acetate, poly (alkyl) methacrylate, copolymers of acrylic or methacrylic acid esters, eudragit, polymethacrylates containing quaternary ammonium group, high molecular weight polyvinyl alcohols, polyvinyl acetate dispersion (Eg. Kollidon), waxes, hydrogenated vegetable oil, fatty acids, long chain fatty alcohols, cellulose acetate butyrate or mixtures thereof and other materials known to one of ordinary skill in the art. Preferably, the water insoluble polymer used in extended release coating is cellulose derivative such as ethyl cellulose and like thereof.

Suitable "plasticizer" may include, but not limited to glycerin, polyethylene glycol, PEG 400, polyethylene glycol monomethyl ether, propylene glycol, sorbitol sorbitan solution or mixtures and like thereof.

The term "acidic coat" mainly comprises of acidic substance, which helps in providing an acidic pH micro-environment between the upper part of the small intestine and the lower part of the large intestine. The acidic pH micro-environment improves solubility and bioavailability of Clozapine. In a preferred embodiment, the acidic coat layer comprises tartaric acid and sodium chloride.

The pharmaceutically acceptable excipient(s) include but are not limited to binders, fillers or diluents, lubricants, osmotic agent, plasticizer, glidants or solvent(s) and mixtures thereof. One excipient can perform more than one function. The excipients may be selected from but are not limited to starches such as potato starch, wheat starch, corn starch; microcrystalline cellulose, celluloses such as hydroxypropyl cellulose, hydroxyethyl cellulose, hydroxypropyl methyl cellulose, ethyl cellulose, sodium carboxy methyl cellulose; polyethylene oxide, polyvinyl pyrrolidone, poly-N-vinyl amide, polyethylene glycol, gelatin, poly propylene glycol, carbohydrates, confectioner's sugar, compressible sugar, dextrates, dextrin, dextrose, fructose, lactitol, mannitol, sucrose, lactose, calcium phosphate dibasic or tribasic, calcium sulphate, magnesium stearate, aluminum stearate or calcium stearate or zinc stearate, glyceryl behenate, mineral oil, sodium stearyl fumarate, stearic acid, talc, silicon dioxide, magnesium trisilicate, powdered cellulose, talc, tribasic calcium phosphate, calcium silicate, magnesium silicate, colloidal silicon dioxide, croscarmellose sodium, povidone, guar gum, magnesium aluminium silicate, sodium alginate, sodium starch glycolate and other materials known to a skilled artisan and combinations thereof.

The solvents that can be used in the present invention include all the solvents well known in the art or their mixtures thereof. The solvents are selected from the group comprising isopropyl alcohol, methylene chloride, dichloromethane, acetonitrile, purified water or mixture thereof.

In another embodiment, the present invention relates to a process for the preparation of a stable pharmaceutical composition of Clozapine in the form of multiparticulates like granules, pellets, beads, spheroids or the likes thereof.

In another embodiment, the present invention relates to a process for preparation of a stable extended release pharmaceutical composition of Clozapine in the form of multiparticulates like granules, pellets, beads, spheroids or the likes thereof comprising:
a) Granules, pellets, beads or spheroids comprising Clozapine,
b) Seal coating with hydrophilic polymer,
c) Acidic coating with acidic substance, and
d) Extended release coating with a water insoluble polymer and a water soluble polymer.

In a preferred embodiment, the stable extended release pharmaceutical composition in the form of pellets for the purpose of the present invention shall comprise:
(i) a core containing Clozapine with pharmaceutically acceptable excipients,
(ii) a first seal coat layer,
(iii) an acidic coat layer,
(iv) a second seal coat layer,
(v) an extended release coat,
(vi) a third seal coat layer.

In another embodiment, the extended release coating composition of Clozapine comprises ethyl cellulose and polyethylene glycol 400. The coating composition comprises polyethylene glycol 400 (PEG400) as water soluble pore former. Polyethylene glycol 400 is in liquid state at room temperature and hygroscopic in nature. Due to this property, Clozapine pellets become cohesive during manufacturing operations and storage. This cohesive nature affects free flow of pellets during capsules filling operations. To reduce the cohesive nature of polyethylene glycol 400 in extended release film, hypromellose seal coat is applied over extended release coat.

The terms "impurity" or "impurities" refer to undesired substance(s) in a composition which may be present in a composition immediately following manufacturing or which may be formed after a certain period of shelf life of a composition. Impurities may be formed via degradation of one or more components of the composition. Sources of degradation can include, e.g., oxidation, light, ultraviolet light, moisture, heat, changes in pH, and composition component interactions. In a preferred embodiment, the composition of the present invention comprise any individual impurity not more than 0.2% that relates to Impurity A, Impurity B, Impurity C, Impurity D and other individual unknown impurity not more than 0.1%

The impurities related to Clozapine for the purpose of the present invention includes Impurity A, Impurity B, Impurity C, Impurity D and single unknown impurity.

The impurities related to Clozapine are as described below:

Impurity A: 8-Chloro-11-(piperazin-1-yl)-5H-dibenzo[b,e][1,4]diazepine.

Impurity B: 1-[2-[(2-Amino-4-chlorophenyl)amino]benzoyl]-4-methylpiperazine.

Impurity C: 8-Chloro-5,10-dihydro-11H-dibenzo[b,e][1,4]diazepin-11-one.

Impurity D: 1,4-Bis(8-chloro-5H-dibenzo[b,e][1,4]diazepin-11-yl)piperazine.

In another embodiment, the present invention relates to a stable extended release pharmaceutical composition of Clozapine, wherein the individual impurity in the pharmaceutical composition is not more than 0.2% w/w of Clozapine upon storage at 40±2° C. and 75±5% RH for 6 months. Further, the total impurities in the pharmaceutical composition is not more than 2% w/w of Clozapine after storage at 40±2° C. and 75±5% RH for 6 months.

In another embodiment, the present invention relates to a stable extended release pharmaceutical composition of Clozapine, wherein assay of Clozapine is from 95% to 105% after storage at 40° C. and 75% RH for 6 months.

In another embodiment the present invention relates to a stable extended release pharmaceutical composition of Clozapine, wherein the composition provides dissolution profile as: (1) not more than 30% weight of Clozapine is dissolved in 30 minutes; (2) between 40% to 70% weight of Clozapine is dissolved in 2 hours; and (3) more than 80% weight of Clozapine is dissolved in 10 hours after storage, wherein the dissolution profile is measured using a USP type I apparatus (basket), placing the composition in 900 mL of acetate buffer having pH 4.5, at 37° C. and 100 rpm.

In another embodiment the present invention relates to a stable extended release pharmaceutical composition of Clozapine, wherein the individual impurity level in the composition is not more than 0.2% w/w of Clozapine upon storage at 25±2° C. and 60±5% RH for 6 months.

In another embodiment the present invention relates to a stable extended release pharmaceutical composition of Clozapine, wherein the total impurities in the pharmaceutical composition is not more than 2% w/w of Clozapine upon storage at 25±2° C. and 60±5% RH for 6 months.

In another embodiment, the present invention relates to a stable extended release pharmaceutical composition of Clozapine, wherein the assay of Clozapine is from 95% to 105% after storage at 25±2° C. and 60±5% RH for 6 months.

In another embodiment, the present invention relates to a stable pharmaceutical composition of Clozapine, wherein the composition comprises Clozapine having an effective average particle size (D90) of less than about 10 micron that provides solubility of at least 20 mg/ml in 0.1 N Hydrochloric acid.

Solubility study of micronized clozapine at various pH and solvent, which can be used for the preparation of stable extended release pharmaceutical composition according to the present invention is summarized in Table 1.

TABLE 1

Solubility

| Sr. No. | Medium | Solubility (mg/ml) | |
| --- | --- | --- | --- |
| | | Un-micronized (D90-NMT 75 Micron) | Micronized (D90-NMT 10 Micron) |
| 1. | 0.1N Hydrochloric acid | 0.418 | 28.727 |
| 2. | pH 4.0 to 4.5 of Acetate buffer | 0.73 | 4.773 |
| 3. | pH 6.8 of Phosphate buffer | 0.100 | 0.121 |
| 4. | Purified Water | 0.040 | 0.031 |

The composition of the invention is suitable for the treatment of schizophrenia patients, thereby reducing the risk of recurrent suicidal behavior in patients with schizophrenia or schizoaffective disorder and Parkinson related psychosis.

EXAMPLES

The following examples are illustrative of the present invention, and the examples should not be considered as limiting the scope of this invention in any way, as these examples and other equivalents thereof will become apparent to those versed in the art, in the light of the present disclosure.

Example 1

Extended Release Pharmaceutical Composition of Clozapine 12.5/25/50/100/200 mg strengths are dose proportional formulations.

TABLE 2

| Formulation components & amounts | |
|---|---|
| Ingredients | Amount (%) |
| Clozapine USP | 20-40 |
| Diluent | 5-35 |
| Binder | 2-10 |
| Seal Coating | 2-20 |
| Acid Coating | 20-40 |
| Extended release coating | 2-20 |
| Glidant | 0.2-2 |

The Clozapine composition can be manufactured by a process as described herein and can be modified using other process steps and equipment generally known in the art. Generally, the process can include a methodology as follows. Sift Clozapine with other excipients through a screen or mesh. Prepare a binder solution. Granulate the dry blend with binder solution. Subsequently apply seal coating solution, acidic coating solution and extended release solution on extrudes or spheroids or granules by using suitable coating equipment. Blend the coated extrudes or spheroids or granules with a suitable glidant.

Example 2

Extended Release Pharmaceutical Composition of Clozapine

TABLE 3

| ER Clozapine formulations | | | | | |
|---|---|---|---|---|---|
| | Theoretical Quantity mg/Capsules | | | | |
| Ingredients | 12.5 | 25 | 50 | 100 | 200 |
| Granulation or Extrusion Spheronization | | | | | |
| Clozapine USP | 12.5 | 25 | 50 | 100 | 200 |
| Microcrystalline Cellulose | 5.375 | 10.75 | 21.5 | 43 | 86 |
| Polyglycol 4000PF (PEG 4000) | 2.125 | 4.25 | 8.5 | 17 | 34 |
| First Seal Coating | | | | | |
| Hypromellose E5 | 1.00 | 2.00 | 4.00 | 8.00 | 16.00 |
| Purified water | q.s. | q.s. | q.s. | q.s. | q.s. |
| Acidic Coating | | | | | |
| Tartaric Acid | 9.375 | 18.75 | 37.5 | 75 | 150 |
| Sodium Chloride | 3.125 | 6.25 | 12.5 | 25 | 50 |
| Purified Water | q.s. | q.s. | q.s. | q.s. | q.s. |
| Second Seal Coating | | | | | |
| Hypromellose E5 | 1.00 | 2.00 | 4.00 | 8.00 | 16.00 |
| Isopropyl alcohol | q.s. | q.s. | q.s. | q.s. | q.s. |
| Dichloromethane | q.s. | q.s. | q.s. | q.s. | q.s. |

TABLE 3-continued

| ER Clozapine formulations | | | | | |
|---|---|---|---|---|---|
| | Theoretical Quantity mg/Capsules | | | | |
| Ingredients | 12.5 | 25 | 50 | 100 | 200 |
| Extended release coating | | | | | |
| Ethyl Cellulose 10 cps | 2.07 | 4.14 | 8.28 | 16.56 | 33.12 |
| PEG 400 | 0.69 | 1.38 | 2.76 | 5.52 | 11.04 |
| Isopropyl alcohol | q.s. | q.s. | q.s. | q.s. | q.s. |
| Dichloromethane | q.s. | q.s. | q.s. | q.s. | q.s. |
| Third Seal Coating | | | | | |
| Hypromellose E5 | 1.125 | 2.25 | 4.5 | 9.00 | 18.00 |
| Isopropyl alcohol | q.s. | q.s. | q.s. | q.s. | q.s. |
| Dichloromethane | q.s. | q.s. | q.s. | q.s. | q.s. |
| Blending | | | | | |
| Talc | 0.365 | 0.73 | 1.46 | 2.92 | 5.84 |
| Cellulose Capsules | Size 4 | Size 4 | Size 3 | Size 1 | Size 00 |
| Theoretical Net Content | 38.75 | 77.50 | 155.00 | 310.00 | 620.00 |

The manufacturing process is described as an illustrative embodiment in accordance with the disclosure. Generally, the process can include methodology as follows. Co-sift Clozapine and microcrystalline cellulose through the sieve (screen or mesh). Granulate the dry blend material with PEG solution in a granulator, or prepare the pellets or spheroids using a spheronizer. Dry the pellets in a suitable processor to apply first seal coating layer in a suitable coating instrument. Apply acidic coat on the seal coated pellets, followed by the second seal coating on the obtained pellets in a suitable coating instrument. Subsequently apply the extended release coating on the obtained seal-coated pellets, followed by the third seal coating on the extended release coated pellets in a suitable coating instrument. Blend seal coated pellets with a suitable glidant. Fill the lubricated pellets in the capsules according to fill weight of each strength.

Example 3

Stability and Dissolution Results of the Extended Release Pharmaceutical Composition of Clozapine The present invention was placed for stability study at long term storage conditions and accelerated storage conditions for evaluation of the stability parameters. The stability results obtained are tabulated below.

Conditions of the Dissolution Bath
Paddle speed: 100 rpm
Temperature of dissolution medium: 37° C.±0.5° C.
Dissolution Medium: pH 4.5 Acetate Buffer
Vessel volume: 900 mL
Time point (hours): 0.5, 2 and 10.
Method:

To the set dissolution apparatus having a 900 mL of dissolution medium as defined above to each of six glass vessels and under the above mentioned conditions, a test sample was added into each basket lower down hood, taking care to exclude the air bubbles from the surface and immediately start the apparatus.

After that, at each time point, 10 mL of the test sample from each of six glass vessels were withdrawn. Then, 2 mL of the aliquot of the test sample were transferred from the collected sample to a single test tube, wherein it was mixed and filtered through 0.45µ polyvinylidene fluoride filter (PVDF filter). Further, the withdrawn volume at each time point is replaced by adding an equal quantity of fresh dissolution medium at 37° C.±0.5° C.

TABLE 4

| | Solubility | | | |
|---|---|---|---|---|
| Condition | Long term (25 ± 2° C. and 60 ± 5% RH) | | | |
| TESTS | LIMITS | INITIAL | 3 Months | 6 Months |
| Water Content | NMT 7.0% w/w | 1.6% w/w | 1.3% w/w | 1.6% w/w |
| | Dissolution ** | | | |
| 0.5 hour | NMT 30% | 15% (14%-17%) | 9% (9%-10%) | 8% (7%-10%) |
| 2 hour | Between 40% to 70% | 53% (49%-56%) | 50% (49% 51%) | 51% (51%-53%) |
| 10 hour | NLT 80% | 95% (94%-97%) | 92% (91%-93%) | 91% (89%-92%) |
| Impurity A | NMT 0.2% | BQL | BQL | BQL |
| Impurity B | NMT 0.2% | BQL | BQL | BQL |
| Impurity C | NMT 0.3% | BQL | BQL | BQL |
| Impurity D | NMT 0.2% | ND | BQL | BQL |
| Any individual unknown impurity | NMT 0.1% | BQL | 0.02% | 0.01% |
| Total impurities | NMT 2% | BQL | 0.03% | 0.03% |
| Assay | 90.0% to 110.0% of label claim | 101.8% | 99.6% | 100.1% |
| Condition | Accelerated (40 ± 2° C. and 75 ± 5% RH) | | | |
| TESTS | LIMITS | INITIAL | 3 Months | 6 Months |
| Water Content | NMT 7.0% w/w | 1.6% w/w | 1.3% w/w | 1.5% w/w |
| | Dissolution | | | |
| 0.5 hour | NMT 30% | 15% (14%-17%) | 9% (7%-10%) | 8% (4%-9%) |
| 2 hour | Between 40% to 70% | 53% (49%-56%) | 49% (48% 50%) | 49% (48%-50%) |
| 10 hour | NLT 80% | 95% (94%-97%) | 91% (90%-92%) | 90% (88%-93%) |
| | Related compounds | | | |
| Impurity A | NMT 0.2% | BQL | 0.02% | 0.02% |
| Impurity B | NMT 0.2% | BQL | BQL | BQL |
| Impurity C | NMT 0.3% | BQL | BQL | BQL |
| Impurity D | NMT 0.2% | ND | 0.02% | 0.02% |
| Any individual unknown impurity | NMT 0.1% | BQL | 0.02% | 0.02% |
| Total impurities | NMT 2% | BQL | 0.06% | 0.07% |
| Assay | 90.0% to 110.0% of label claim | 101.8% | 97.7% | 101.4% |

Below quantification limit for impurity A: 0.012%
Below quantification limit for impurity B: 0.012%
Below quantification limit for impurity C: 0.012%
Below quantification limit for impurity D: 0.012%
Below quantification limit for any individual unknown impurity: 0.012%

From the above stability data, it can be concluded that the pharmaceutical composition of the present invention provides improved stability of Clozapine.

We claim:

1. A stable extended release pharmaceutical composition of Clozapine with one or more pharmaceutically acceptable excipients, comprising: a) granules, pellets, beads or spheroids comprising Clozapine with pharmaceutically acceptable excipients, b) a first seal coat layer comprising a hydrophilic polymer, c) an acidic coating comprising an acidic substance, d) a second seal coat layer comprising a hydrophilic polymer, (e) an extended release coating with a water insoluble polymer and a water soluble polymer, and (f) a third seal coat layer comprising a hydrophilic polymer,
wherein, the amount of the seal coating in the composition is from 2-20%; the amount of the acidic coating in the composition is from 20-40%; the amount of extended release coating in the composition is from 2-20%;
wherein, the hydrophilic polymer comprises hydroxypropyl methylcellulose, hydroxyethyl cellulose, hydroxypropyl cellulose, hydroxyethyl methylcellulose, carboxymethylcellulose, polyethylene glycol, polyethylene oxides, or polyalcohols; the water insoluble polymer comprises Chitosan, polyurethanes, ethyl cellulose, cellulose acetate or waxes; and the water soluble polymer comprises hydroxypropyl methylcellulose, hydroxyethyl cellulose, hydroxypropyl cellulose, hydroxyethyl methylcellulose, carboxymethylcellulose, polyethylene glycol, polyethylene oxides, or polyalcohols;
wherein the total impurities in the said pharmaceutical composition is not more than 2% w/w of Clozapine and wherein an assay of the quantity of Clozapine in the said pharmaceutical composition is from 95% to 105% upon storage at 40±2° C. and 75±5% relative humidity (RH) for 6 months, relative to the quantity of Clozapine in the pharmaceutical composition prior to storage; and wherein the said composition comprises Clozapine having an effective particle size (D90) of less than about 10 micron that provides solubility of Clozapine of at least 20 mg/ml in 0.1N hydrochloric acid.

2. The stable extended release pharmaceutical composition of Clozapine with one or more pharmaceutically acceptable excipients as claimed in claim 1, wherein the individual impurity level in the said pharmaceutical composition is not more than 0.2% w/w of Clozapine upon storage at 40±2° C. and 75±5% RH for 6 months.

3. A stable extended release pharmaceutical composition of Clozapine with one or more pharmaceutically acceptable excipients, comprising: a) granules, pellets, beads or spheroids comprising Clozapine with pharmaceutically acceptable excipients, b) a first seal coat layer comprising a hydrophilic polymer, c) an acidic coating comprising an acidic substance, d) a second seal coat layer comprising a hydrophilic polymer, (e) an extended release coating with a water insoluble polymer and a water soluble polymer, and (f) a third seal coat layer comprising a hydrophilic polymer;
 wherein, the amount of the seal coating in the composition is from 2-20%; the amount of the acidic coating in the composition is from 20-40%; the amount of extended release coating in the composition is from 2-20%;
 wherein, the hydrophilic polymer comprises hydroxypropyl methylcellulose, hydroxyethyl cellulose, hydroxypropyl cellulose, hydroxyethyl methylcellulose, carboyxmethylcellulose, polyethylene glycol, polyethylene oxides, or polyalcohols; the water insoluble polymer comprises Chitosan, polyurethanes, ethyl cellulose, cellulose acetate or waxes; the water soluble polymer comprises hydroxypropyl methylcellulose, hydroxyethyl cellulose, hydroxypropyl cellulose, hydroxyethyl methylcellulose, carboxymethylcellulose, polyethylene glycol, polyethylene oxides, or polyalcohols,
 wherein the total impurities in the said pharmaceutical composition is not more than 2% w/w of Clozapine and wherein an assay of the quantity of Clozapine in the said pharmaceutical composition is from 95% to 105% upon storage at 25±2° C. and 60±5% RH for 6 months, relative to the quantity of Clozapine in the pharmaceutical composition prior to storage; and
 wherein the said composition comprises Clozapine having an effective particle size (D90) of less than about 10 micron that provides solubility of Clozapine of at least 20 mg/ml in 0.1N hydrochloric acid.

4. The stable extended release pharmaceutical composition of Clozapine with one or more pharmaceutically acceptable excipients as claimed in claim 3, wherein the individual impurity level in the said pharmaceutical composition is not more than 0.2% w/w of Clozapine upon storage at 25±2° C. and 60±5% RH for 6 months.

5. A stable extended release pharmaceutical composition comprising Clozapine with one or more pharmaceutically acceptable excipients, wherein the said composition provides dissolution profile as: (1) not more than 30% weight of Clozapine is dissolved in 30 minutes; (2) between 40% to 70% weight of Clozapine is dissolved in 2 hours; and (3) more than 80% weight of Clozapine is dissolved in 10 hours, wherein the dissolution profile is measured using a USP type I apparatus (basket), placing the composition in 900 ml of acetate buffer having pH 4.5 at 37° C. and 100 rpm.

6. The stable extended release pharmaceutical composition comprising Clozapine with one or more pharmaceutically acceptable excipients as claimed in claim 5, wherein the said pharmaceutical composition is compressed in the form of tablets or mini-tablets, or filled in capsules to provide the pharmaceutical composition of Clozapine for oral administration.

7. The stable extended release pharmaceutical composition comprising Clozapine with one or more pharmaceutically acceptable excipients as claimed in claim 3, where in the said composition provides dissolution profile as: (1) not more than 30% weight of Clozapine is dissolved in 30 minutes; (2) between 40% to 70% weight of Clozapine is dissolved in 2 hours; and (3) more than 80% weight of Clozapine is dissolved in 10 hours, wherein the dissolution profile is measured using a USP type I apparatus (basket), placing the composition in 900 ml of acetate buffer having pH 4.5 at 37° C. and 100 rpm.

8. The stable extended release pharmaceutical composition comprising Clozapine with one or more pharmaceutically acceptable excipients as claimed in claim 7, wherein the said pharmaceutical composition is compressed in the form of tablets or mini-tablets, or filled in capsules to provide the pharmaceutical composition of Clozapine for oral administration.

\* \* \* \* \*